United States Patent
Zhou (10) Patent No.: US 7,662,652 B2
(45) Date of Patent: Feb. 16, 2010

(54) CHEMICAL SENSOR USING SEMICONDUCTING METAL OXIDE NANOWIRES

(75) Inventor: Chongwu Zhou, Rowland Heights, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 12/166,302

(22) Filed: Jul. 1, 2008

(65) Prior Publication Data

US 2008/0261342 A1 Oct. 23, 2008

Related U.S. Application Data

(62) Division of application No. 11/077,164, filed on Mar. 9, 2005, now Pat. No. 7,394,118.

(60) Provisional application No. 60/551,840, filed on Mar. 9, 2004.

(51) Int. Cl.
*H01L 21/64* (2006.01)
*H01L 23/18* (2006.01)

(52) U.S. Cl. .................. 438/49; 438/565; 438/507; 438/510

(58) Field of Classification Search .......... 438/49, 438/565, 507, 510
See application file for complete search history.

(56) References Cited

U.S. PATENT DOCUMENTS

| | | | |
|---|---|---|---|
| 5,624,640 A | 4/1997 | Potthast et al. | |
| 7,294,417 B2 * | 11/2007 | Ren et al. | 428/701 |
| 7,394,118 B2 | 7/2008 | Zhou | |
| 2002/0118027 A1 | 8/2002 | Routkevitch et al. | |
| 2003/0089899 A1 * | 5/2003 | Lieber et al. | 257/9 |
| 2003/0121764 A1 | 7/2003 | Yang et al. | |
| 2004/0005723 A1 | 1/2004 | Empedocles et al. | |
| 2004/0105810 A1 | 6/2004 | Ren et al. | |
| 2005/0097941 A1 | 5/2005 | Sandvik et al. | |
| 2005/0221072 A1 * | 10/2005 | Dubrow et al. | 428/292.1 |

OTHER PUBLICATIONS

Alivisatos, A.P., "Semiconductor Clusters, Nanocrystals, and Quantum Dots", *Science*, 271(5251):933-937, Feb. 1996.
Bellingham, J.R., et al., "Precise measurements of oxygen content: Oxygen vacancies in transparent conducting indium oxide films", *Appl. Phys. Lett.*, 58(22):2506-2508, Jun. 1991.
Chen, C., et al., "Large-scale catalytic synthesis of crystalline gallium nitride nanowires", *Adv. Mater.*, 12(10):738-741, (2000).

(Continued)

*Primary Examiner*—Ngan Ngo
*Assistant Examiner*—Benjamin Tzu-Hung Liu
(74) *Attorney, Agent, or Firm*—Fish & Richardson P.C.

(57) ABSTRACT

Indium oxide nanowires are used for determining information about different chemicals or Biologics. Chemicals are absorbed to the surface of the nanowires, and cause the semiconducting characteristics of the Nanowires to change. These changed characteristics are sensed, and used to determine either the presence of the materials and/or the concentration of the materials. The nanowires may be between 10 and 30 nm in diameter, formed using a comparable size particle of catalyst material. The nanowires may then be used as part of the channel of a field effect transistor, and the field effect transistor is itself characterized.

10 Claims, 6 Drawing Sheets

OTHER PUBLICATIONS

Chung, W.Y., et al., "Preparation of indium oxide film by spin-coating method and its gas-sensing properties", *Sensors and Actuators B*, 46, 139-145, (1998).

Comini, E., et al., "Light enhanced gas sensing properties of indium oxide and tin dioxide sensors", *Sensors and Actuators B*, 65, 260-263, (2000).

Comini, E., et al., "Stable and highly sensitive gas sensors based on semiconducting oxide nanobelts", *Appl. Phys. Lett.*, 81(10):1869-1871, Sep. 2002.

Cui, Y., et al., "Diameter-controlled synthesis of single-crystal silicon nanowires", *Appl. Phys. Lett.*, 78(15):2214-2216, Apr. 2001.

Cui, Y., et al., "Doping and electrical transport in silicon nanowires", *J. of Physical Chemistry B*, 104(22):5213-5216, Jun. 2000.

Cui, Y., et al., "High performance silicon nanowire field effect transistors", *Nano Letters*, 3(2):149-152, (2003).

Cui, Y., et al., "Nanowire nanosensors for highly sensitive and selective detection of biological and chemical species", *Science*, 293(5533):1289-1292, Aug. 2001.

Duan, X., et al., "General synthesis of compound semiconductor nanowires", *Adv. Mater.*, 12(4):298-302, (2000).

Duan, X., et al., "Indium phosphide nanowires as building blocks for nanoscale electronic and optoelectronic devices", *Nature*, 409, 66-69, Jan. 2001.

Duan, X., et al., "Laser-assisted catalytic growth of single crystal GaN nanowires", *J. Am. Chem. Soc.*, 122(1):188-189, (2000).

Duan, X., et al., "Single-nanowire electrically driven lasers", *Nature*, 421, 241-245, Jan. 2003.

Gagaoudakis, E., et al., "The influence of deposition parameters on room temperature ozone sensing properties of $InO_x$, films", *Sens. Actuators B*, 80, 155-161, (2001).

Hoheisel, W., et al., "Desorption stimulated by laser-induced surface-plasmon excitation", *Phys. Rev. Lett.*, 60(16):1649-1652, Apr. 1988.

Hu, J., et al., "Chemistry and physics in one dimension: synthesis and properties of nanowires and nanotubes", *Acc. Chem. Res.*, 32(5):435-445, (1999).

Huang, M.H., et al., "Catalytic growth of zinc oxide nanowires by vapor transport", *Adv. Mater.*, 13(2):113-116, Jan. 2001.

Huang, Y., et al., "Logic gates and computation from assembled nanowire building blocks", *Science*, 294(5545):1313-1317, Nov. 2001.

Huang, Y., et al., "Room-temperature ultraviolet nanowire nanolasers", *Science*, 292(5523):1897-1899, Jun. 2001.

Kiriakidis, G., et al., "Ozone sensing properties of polycrystalline indium oxide films at room temperature", *Phys. Status Solidi A*, 185(1):27-32, (2001).

Kong, J., et al., "Full and modulated chemical gating of individual carbon nanotubes by organic amine compounds", *J. Phys. Chem. B*, 105(15):2890-2893, (2001).

Kong, J., et al., "Functionalized carbon nanotubes for molecular hydrogen sensors", *Adv. Mater.*, 13(18):1384-1386, Sep. 2001.

Kong, J., et al., "Nanotube molecular wires as chemical sensors", *Science*, 287(5453):622-625, Jan. 2000.

Kong, J., et al., "Synthesis, integration, and electrical properties of individual single-walled carbon nanotube", *Appl. Phys. A*, 69, 305-308, (1999).

Law, M., et al., "Photochemical sensing of $NO_2$ with $SnO_2$ nanoribbon nanosensors at room temperature", *Angew. Chem. Int. Ed.*, 41(13):2405-2408, (2002).

Lee, H., et al., "Enhancement of CO sensitivity of indium oxide-based semiconductor gas sensor through ultra-thin cobalt adsorption", *Sens. Actuators B*, 79, 200-205, (2001).

Li, C., et al., "Chemical gating of $In_2O_3$ nanowires by organic and biomolecules", *Applied Physics Letters*, 83(19):4014-4016, Nov. 2003.

Li, C., et al., "Diameter-controlled growth of single-crystalline $In_2O_3$ nanowires and their electronic properties", *Adv. Mater.*, 15(2):143-146, Jan. 2003.

Li, C., et al., "$In_2O_3$ nanowires as chemical sensors", *Applied Physics Letters*, 82(10):1613-1615, Mar. 2003.

Li, C., et al., "Surface treatment and doping dependence of $In_2O_3$ nanowires as ammonia sensors", *J. Phys. Chem. B*, 107(45):12451-12455, (2003).

Li, C., et al., "Synthesis, electronic properties, and applications of indium oxide nanowires", *Ann. N.Y. Acad. Sci.*, 1006, 104-121, (2003).

Liess, M., "Electric-field-induced migration of chemisorbed gas molecules on a sensitive film—a new chemical sensor", *Thin Solid Films*, 410, 183-187, (2002).

Liu, X., et al., "Carbon nanotube field-effect inverters", *Appl. Phys. Lett.*, 79(20):3329-3331, Nov. 2001.

Martel, R., et al., "Single- and multi-wall carbon nanotube field-effect transistors", *Appl. Phys. Lett.*, 73(17):2447-2449, Oct. 1998.

Morales, A.M., et al., "A laser ablation method for the synthesis of crystalline semiconductors nanowires", *Science*, 279(5348):208-211, Jan. 1998.

Nanto, H., et al., "Zinc-oxide thin-film ammonia gas sensors with high sensitivity and excellent selectivity", *J. Appl. Phys.*, 60(2):482-484, Jul. 1986.

Pan, Z., et al., "Nanobelts of semiconducting oxides", *Science*, 291, 1947-1949, Mar. 2001.

Peng, X., et al., "Synthesis and photoluminescence of single-crystalline $In_2O_3$ nanowires", *J. Mater. Chem.*, 12, 1602-1605, (2002).

Qi, P., et al., "Toward large arrays of multiplex functionalized carbon nanotube sensors for highly sensitive and selective molecular detection", *Nano Letters*, 3(3)347-351, (2003).

Rusu, C., et al., "Defect sites on $TiO_2$(110). Detection by $O_2$ photodesorption" *Langmuir*, 13(16):4311-4316, (1997).

Sevanian, A., et al., "Low-density lipoprotein (LDL) modification: basic concepts and relationship to atherosclerosis", *Blood Purification*, 17(2-3):66-78, (1999).

Shigesato, Y., et al., "Electrical and structural properties of low resistivity tin-doped indium oxide films", *J. Appl. Phys.*, 71(7):3356-3364, Apr. 1992.

Shimizu, Y., et al., "Basic aspects and challenges of semiconductor gas sensors", *MRS Bulletin*, 24(6):18-24, Jun. 1999.

Sreenivas, K., et al., "Preparation and characterization of rf sputtered indium tin oxide films", *J. Appl. Phys.*, 57(2):384-392, Jan. 1985.

Strassler, S., et al., "Simple models for n-type metal oxide gas sensors", *Sens. Actuators*, 4, 465-472, (1983).

Sze, S.M., et al., *Physics of Semiconductor Devices*, Second Ed., John Wiley & Sons, Inc., New York, 1981, Table of Contents only, 6 pages.

Tamaki, J., et al., "Sensing properties to dilute chlorine gas of indium oxide based thin film sensors prepared by electron beam evaporation", *Sens. Actuators B*, 83, 190-194, (2002).

Williams, D.E., "Semiconducting oxides as gas-sensitive resistors", *Sens. Actuators B*, 57, 1-16, (1999).

Wu, Y., et al., "Germanium nanowire growth via simple vapor transport", *Chem. Mater.*, 12(3):605-607, (2000).

Wyckoff, R.W.G., *Crystal Structures: Volume 4*, Second Ed., Interscience Publishers, New York 1968, Table of Contents only, 3 pages.

Yang, H., et al., "One-step nanocasting synthesis of highly ordered single crystalline indium oxide nanowire arrays from mesostructured frameworks", *J. Am. Chem. Soc.*, 125(16):4724-4725, (2003).

Zhang, D., "Electronic transport studies of single-crystalline $In_2O_3$ nanowires", *Appl. Phys. Lett.*, 82(1):112-114, Jan. 2003.

Zhang, D., et al., "Doping dependent $NH_3$ sensing of indium oxide nanowires", *Appl. Phys. Lett.*, 83(9):1845-1847, Sep. 2003.

Zhang, D., et al., "Ultraviolet photodetection properties of indium oxide nanowires", *Appl. Phys. A: Mater. Sci. Process*, 77, 163-166, (2003).

Zheng, M.J., et al., "Ordered indium-oxide nanowire arrays and their photoluminescence properties", *Appl. Phys. Lett.*, 79(6):839-841, Aug. 2001.

Zhou, C., et al., "Electrical measurements of individual semiconducting single-walled carbon nanotubes of various diameters", *Appl. Phys. Lett.*, 76(12):1597-1599, Mar. 2000.

Zhou, C., et al., "Modulated chemical doping of individual carbon nanotubes", *Science*, 290(5496):1552-1555, Nov. 2000.

\* cited by examiner

CHEMICAL SENSOR USING SEMICONDUCTING METAL OXIDE NANOWIRES

This application is a divisional application of and claims priority to U.S. patent application Ser. No. 11/077,164, filed Mar. 9, 2005 now U.S. Pat. No. 7,394,118, which claims the benefit of the priority of U.S. Provisional Application Ser. No. 60/551,840, filed Mar. 9, 2004 and entitled "CHEMICAL SENSING AND BIO-SENSING APPLICATIONS OF INDIUM OXIDE NANOWIRES", the disclosures of which are hereby incorporated by reference.

FEDERALLY SPONSORED RESEARCH OR DEVELOPMENT

This invention was made with government support under Contract No. ECS0132982 awarded by the National Science Foundation. The government has certain rights in the invention.

BACKGROUND

Semiconducting metal oxides have been used for chemical sensing.

Indium oxide, or $In_2O_3$ has been found to have advantageous sensitivities to certain gases, such as $O_3$, $Cl_2$, $NO_2$, $NH_3$, CO and $H_2$ when used as a sensor. Sensors of this type may be characterized in terms of their sensitivity. The sensitivity of a sensor is defined as the ratio of the resistance of the sensor after exposure, divided by the resistance of the sensor prior to exposure. The sensitivity of indium oxide thin-film devices may be around 58% for diluted $NO_2$ gas, with a response time of several minutes.

Thin-film sensing devices have inherent limitations. These devices may have a limited maximum sensitivity based on the limited surface to volume ratio for the thin films. Moreover, many of these thin-film devices are intended to be operated at high temperatures, for example, 200 to 600° C. These high temperatures may enhance the chemical reactivity between the sensor materials and the surrounding gases. However, this high temperature requirement may be inconvenient for many applications.

SUMMARY

The present application describes formation and use of metal oxide semiconductors which are formed to have a very large aspect ratio—here connoting a ratio between the length and width. One aspect uses metal oxide semiconductors which are shaped as nanowires. In embodiments, the nanowires may be used in a sensor to detect materials—e.g., chemical or biological elements.

The metal oxide semiconductor may be an indium oxide, such as $In_2O_3$. The aspect ratio may be, for example, 10 nm/5 um=$2\times10^{-3}$; or 30 nm/3 um=$10\times10^{-3}$.

An aspect forms indium oxide nanowires into a chemical sensor, and uses this sensor to detect the presence and/or concentration of materials, e.g., chemical species and/or biochemical species. The materials may include compounds including $NO_2$ and $NH_3$. Biochemical species may include low density lipoproteins, DNA, and various other proteins. This may be used in healthcare and medicine studies.

Another aspect uses the nanowires in an active device to detect presence and concentration of electron donating or electron removing materials.

BRIEF DESCRIPTION OF THE DRAWINGS

These and other aspects will now be described in detail with reference to the accompanying drawings, wherein.

DETAILED DESCRIPTION

An embodiment forms nanowires from a semiconducting metal oxide material. In the embodiment, the nanowires can be any structure with a thickness less than 50 nm. The structure need not be cylindrical, although in many embodiments the structure will approximate a cylindrical shape, and the "thickness" will be the diameter of the cylinder. The relatively small diameter nanowire has a very large aspect ratio between its length and width, e.g. an aspect ratio of 100:1. These devices may therefore be approximated as effectively one dimensional structures, which have a very high surface to volume ratio.

An embodiment uses indium oxide as the semiconducting metal oxide material. The nanowires may be used for various kinds of detection.

The nanowires according to an embodiment may be between 8 and 30 nm in diameter. The smallest size nanowires may be between 8 and 12 nm in diameter. The nanowires may be formed of indium oxide, e.g., $In_xO_y$. A preferred material may be $In_2O_3$, which is a wide band gap semiconductor that has a direct band gap of about 3.6 electron volts and in indirect band gap of about 2.5 electron volts.

Chemicals may be adsorbed on the surface of the nanowires. The adsorbed chemicals may cause depletion or enrichment of charge carriers on the surface. In an embodiment, the device may have on-off ratios of $10^6$ for $NO_2$, and $10^5$ for $NH_3$. This may be much better then thin-film based sensors, for example as much as four to five orders of magnitude improved.

The embodiment may also allow sensors to have short response times. The response time is defined as the time duration for the resistance of the sensor to change by one order of magnitude. For example, the response time may be 5 seconds for 100 ppm $NO_2$ and 10 seconds for 1% $NH_3$.

These sensors are also quite sensitive; being capable of detecting 0.5 ppm for $NO_2$ and 0.02% for $NH_3$.

Another aspect uses ultraviolet light as a cleanser for the chemical sensor, which may allow the recovery in a short time, so that the chemical sensor can be used again.

In one embodiment, the indium oxide nanowires have highly uniform geometries. One aspect may use such wires which are in the single crystalline form.

I. Wire Formation

Many different techniques can be used to form the nanowires.

The wires may be formed using electrodeposition of Indium into an anodized alumina template with subsequent oxidation. Another technique may use a rapid heating process to grow the indium oxide nanowires from indium grains in a mixture of argon and oxygen. A vapor-liquid-solid growth technique may be used in which the nanowire diameters are controlled by catalyst nanoparticle size. Another technique may use a template assisted approach with porous silica.

Figure 1:
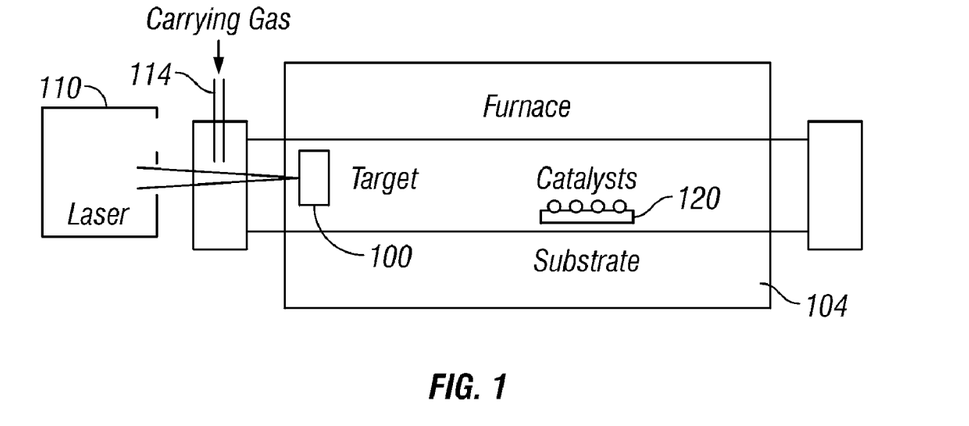
FIG. 1 shows a furnace operating to form indium oxide nanowires.

FIG. 1 shows a schematic diagram of a laser assisted chemical vapor deposition system for forming the nanowires using the vapor-liquid-solid mechanism. Indium vapor is generated by laser ablation of an indium containing target. Monodisperse gold clusters are used as the catalyst.

FIG. 1 shows an InAs target 100 located in a furnace at a first end 104. The furnace may be formed from a quartz tube. A laser 110 produces an output beam 112 that is directed at the target 100. The laser effect on the target creates Indium vapor. An argon carrying gas is supplied through port 114. The carrying gas may be a stream of argon mixed with 0.02% oxygen. The carrying gas carries the indium gas toward the substrate 120.

The substrate may be a $Si/SiO_2$ substrate with catalyst particles thereon. The catalyst particles may include clusters of Au on the surface of the substrate. The substrate itself may be located toward the downstream end of the furnace where it collects the particles of Indium.

In the embodiment, the pressure inside the furnace is maintained at 220 torr at a temperature of 770° C.

Figure 2:
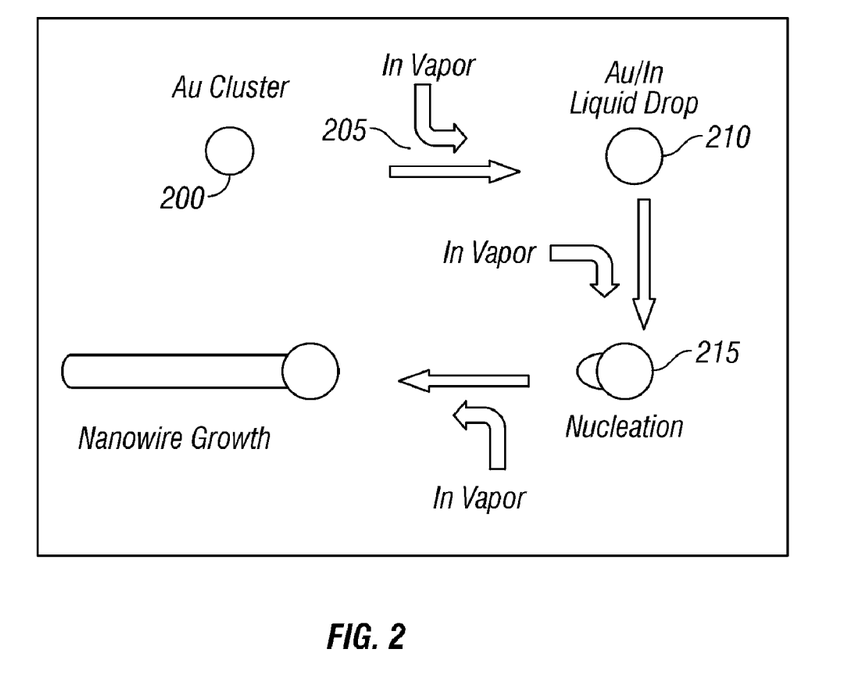
FIG. 2 shows a growth curve of the nanowires from three-phases.

The operation process follows the well-known vapor-liquid-solid mechanism which is illustrated in FIG. 2. FIG. 2 illustrates the Au cluster 200 which is brought into contact with the indium atoms in the vapor phase at 205 to form an Au/In liquid drop 210. The liquid drop 210 remains in contact with the indium vapor, which is brought to beyond supersaturation, shown as nucleation 215. The continued contact of indium beyond supersaturation causes outgrowth of In and its reaction with oxygen at a high temperature, to form single crystalline $In_2O_3$ nanowires.

Figure 3:
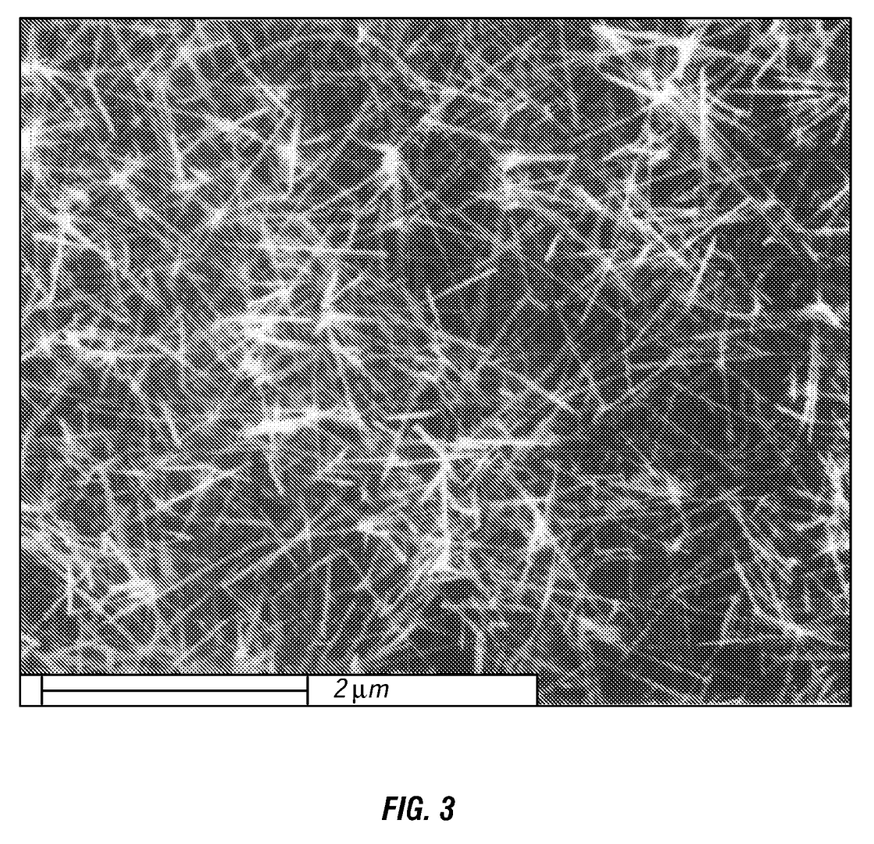
FIG. 3 shows a view of nanowires grown by laser ablation on a substrate.

FIG. 3 shows a typical scanning electron microscope image of indium oxide nanowires grown on an $Si/SiO_2$ substrate with evaporated Au thin film as catalysts. The nanowires, as shown in FIG. 3 may cover the substrate and appear as straight wires.

A catalyst of one or many monodisperse gold clusters, each of nanometer-scale sizes, can produce small and more uniform sized nanowires. These "nano clusters" of catalyst are used on a silicon substrate. Preferably the nano clusters are distributed uniformly over the surface of the substrate. The laser ablation technique is then used to form indium oxide nanowires that have diameters of similar sizes to the sizes of the catalyst particles.

Figure 4:
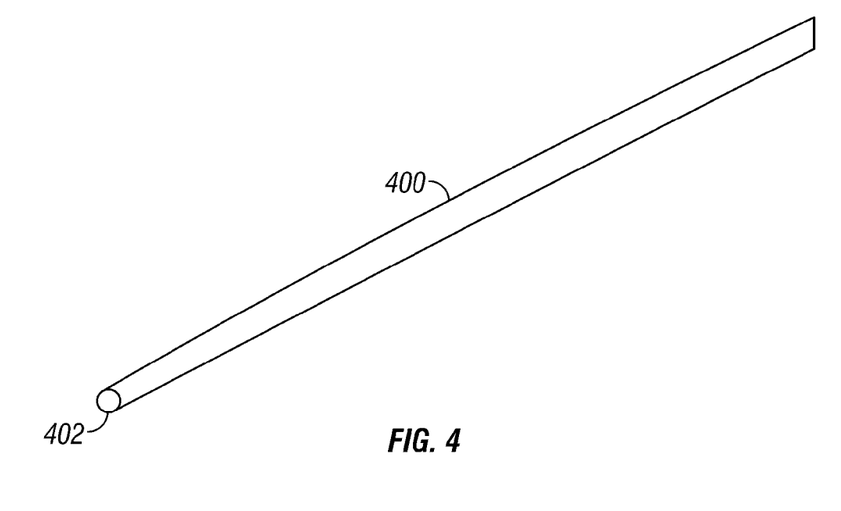
FIG. 4 shows the way in which the nanowire is attached to and takes its shape from a particle of catalyst.

FIG. 4 shows a single indium oxide nanowire 400 made from a 10 nm gold cluster 402. The gold/indium alloy particle 402 has a diameter of about 10 nm at the end of the nanowire 400. The vapor-liquid-solid growth mechanism produces a mostly homogeneous particle without substantial domain boundaries. The nanowire 400 that is formed has a diameter which is consistent with the diameter of the catalytic particle 402 thereby producing a nanowire of approximately 10 nm, e.g., within 20% or 10% or 5% of the catalyst size as explained below. The wire is also extremely crystalline. Exemplary analysis shows that the nanowire has a cubic crystal structure with a lattice constant of approximately 1.03 nm. This is consistent with the lattice constant of bulk indium oxide which is 1.01 nm. Nanowire growth direction is in the <110> direction, with a lattice spacing consistent with the lattice constant. For example, the lattice spacing was measured to be 0.72 nm along the 110 direction. Importantly, this formation technique forms no native oxide layer outside the nanowire, which may further improve its characteristics.

Figure 5A:
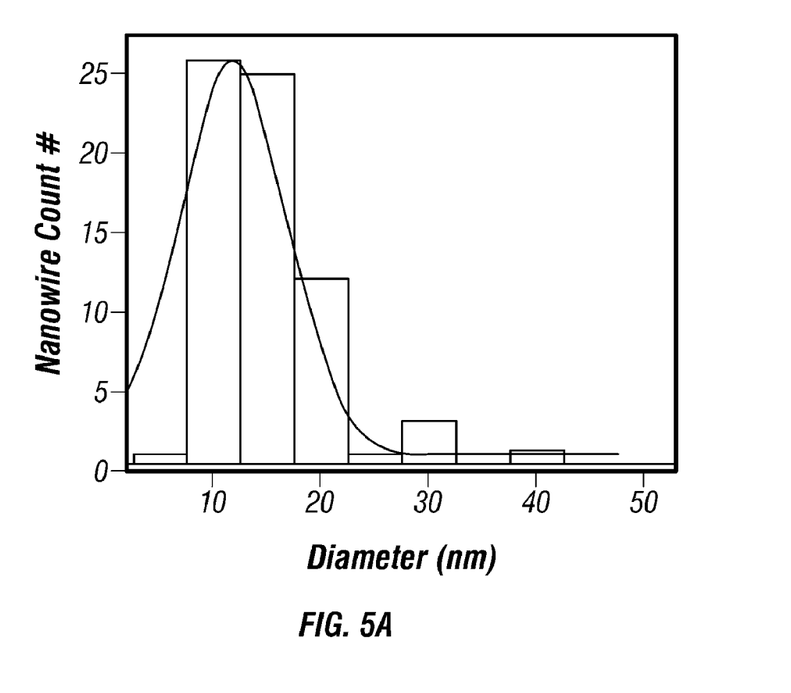
FIGS. 5A-5C show distribution curves for sizes of nanowires which are grown for different size catalyst particles.
Figure 5B:
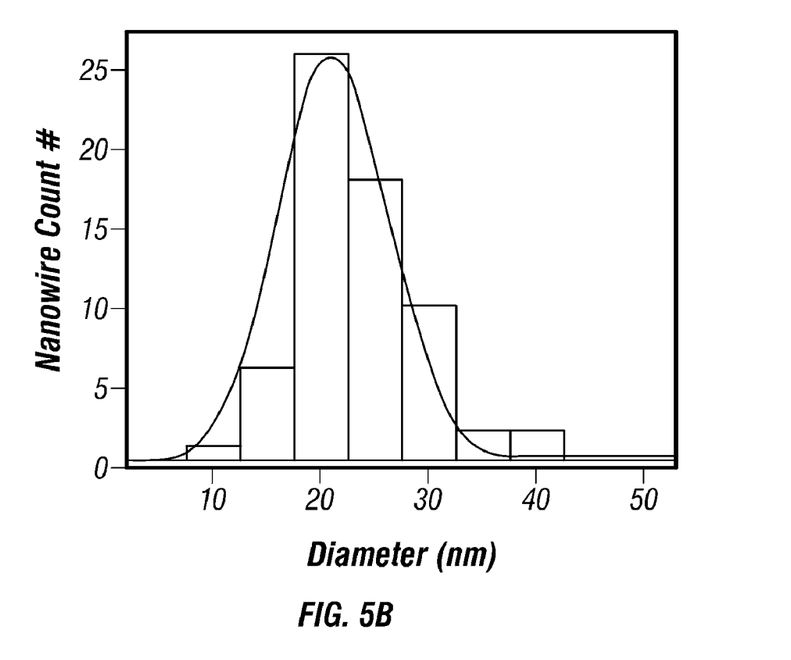
Figure 5C:
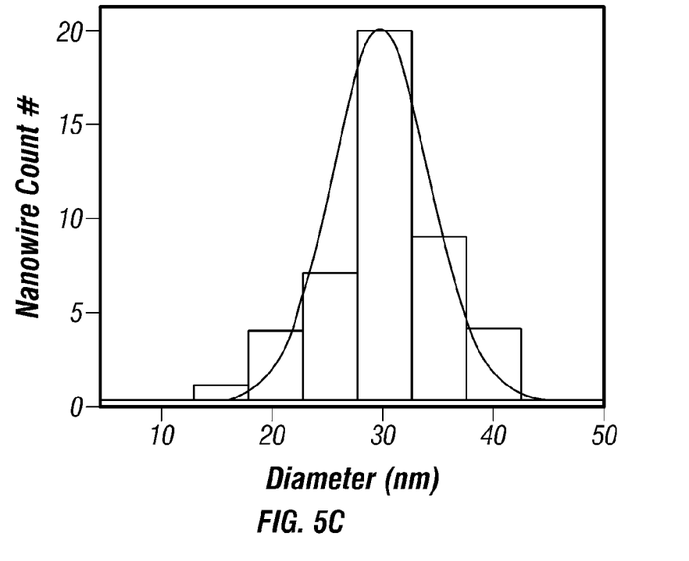

Other aspects establish diameter controlled growth of indium oxide nanowires using different kinds of gold clusters. In different embodiments, gold clusters are used of 10+/−1.5 nm; 20+/−2.0 nm, and 30+/−3.0 nm. FIGS. 5a, 5b and 5c respectively show charts of the sizes of the indium oxide nanowires grown from these clusters. There is a direct connection between the size of the catalytic particle and the diameter of the nanowire which is produced. The distribution of formed nanowires is distributed according to a Gaussian. For example, the first size gold cluster of 10+/−1.5 nm produces a mean nanowire diameter of 10.9+/−1.1 nm. Similarly, the second gold cluster of 20+/−2.0 nm produces a mean nanowire diameter of 20.6+/−2.5 nm. The gold cluster of 30+/−3.0 nm produces a nanowire diameter of 30.1+/−2.4 nm respectively. This demonstrates that the width of the nanowire mirrors the colloidal catalyst particle size within a few nanometers.

The formation method may produce indium oxide nanowires with diameters of around 10 nm and lengths of about 2-6 μm, e.g. a length of 5 μm.

This technique enables producing nanowires of small and uniform diameters. This may be important for certain fundamental studies such as electronic properties. For example, indium oxide is known to be a non-stoichiometric type semiconductor in its bulk form due to various parameters including oxygen vacancies.

II. Sensor

Figure 6:
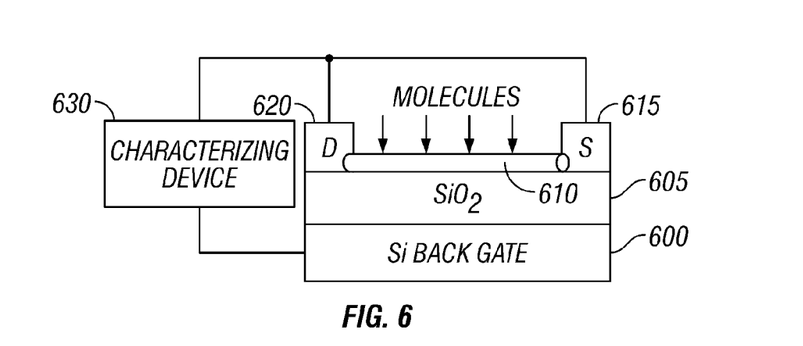
FIG. 6 shows the nanowires being used in a field effect transistor as a sensor.

Another embodiment uses an indium oxide nanowire to form an Indium oxide nanowire field effect transistor shown in FIG. 6. A degeneratively doped silicon wafer 600 is covered with 500 nm of silicon dioxide 605. At least one indium oxide nanowire 610 is deposited over the $SiO_2$ layer 605. A source contact 615 is placed in contact with one end of the nanowire 610. A drain contact 620 is placed in contact with the other end of the nanowire 610. These contacts may be titanium and gold contacts, patterned via photolithography. In an embodiment, the nanowires may be 3 μm in length, and hence the field effect transistor which is formed may correspondingly have a channel length of 3 μm between the source and drain electrodes. The silicon substrate 610 is used as a back gate. Nanowires with smaller diameters exhibit weaker gate dependence and lower transconductance as a result of the finite penetration depth of the gate electric field. In an embodiment, this field effect transistor is formed using nanowires of about 10 nm in diameter. Smaller nanowires, of this type, may exhibit stronger gate dependence and lower transconductance, for example as a result of the finite penetration depth of the gate electric field.

Figure 7:
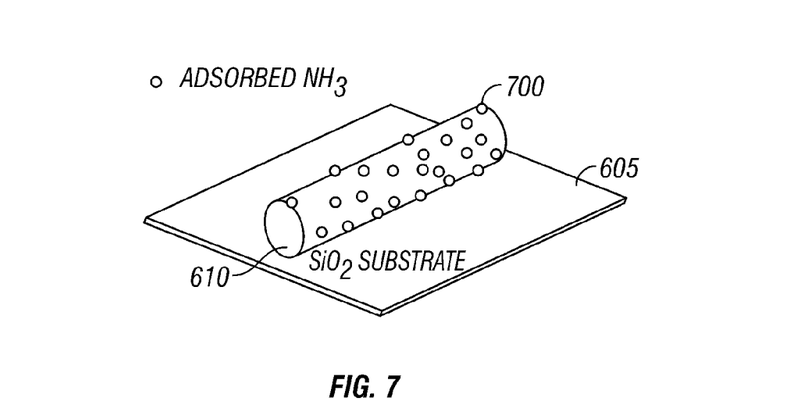
FIG. 7 shows how different materials can be adsorbed on the surface of the nanowire.

FIG. 7 illustrates the nanowire 610 on the $SiO_2$ substrate 605, and how this can be used for chemical sensing measurements in the presence of chemicals which can adsorb on the surface. These chemicals are adsorbed as shown in FIG. 7. FIG. 7 shows a plurality of dots such as 700 of adsorbed $NH_3$ on the surface of the nanowire. The adsorbed $NH_3$ effects the gate electric field by operating as a charge trap. Different materials may affect the gate electric field in different ways.

In an embodiment, these materials may deplete or enrich charge carriers on the surface of the nanowire.

This device has a single Indium oxide nanowire formed between source and drain electrodes using a silicon substrate as a back gate. The indium oxide nanowire device exhibits typical n type transistor characteristics. I-V curves may be recorded before and after exposure to a material to be sensed. The current dependence of the gate bias depends on the exposure to the material being sensed.

In an embodiment, the characteristics of the transistor formed in this way are used to detect materials, including amine or nitro groups, or any chemical, substance or biological material including amine or Nitro groups. These nanowires may operate as chemical sensors at room temperature.

An embodiment detects either $NO_2$ at between 0.5 and 100 ppm or $NH_3$ at between 0.02% to 1% in either argon or dry air. Element 630 is a characterizing element which is connected to the drain, source, and back gate 600. This may be as simple as a voltage source and/or current source and meter, or may be as complicated as a microcontroller or computer running an automated test sequence to characterize the transistor characteristics. The characterizing elements 630 analyze the I-V characteristics of the transistor before and after exposure to the element to be sensed.

Figure 8A:
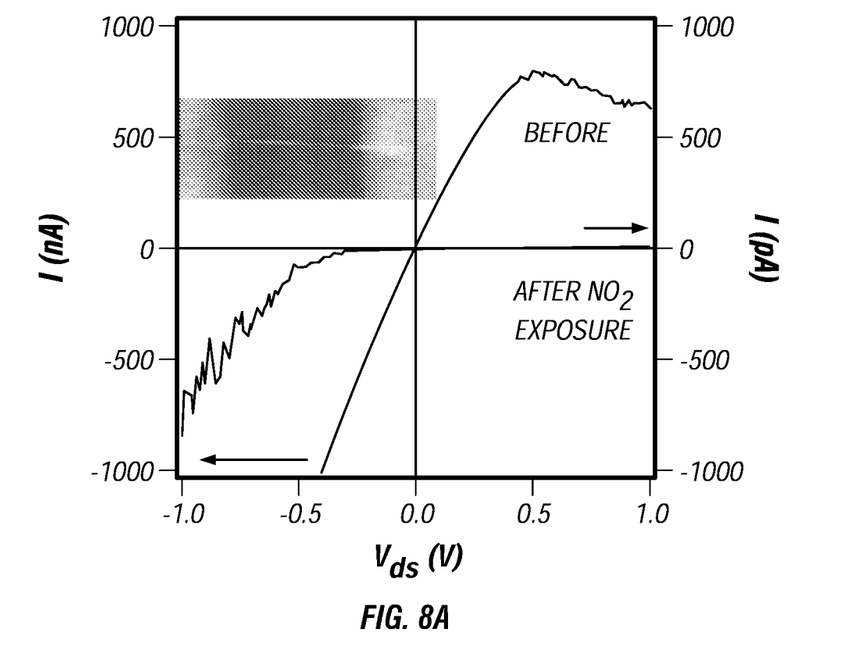
FIGS. 8A and 8B illustrate different curves representing the response of the transistor based on the presence of different chemical species.
Figure 8B:
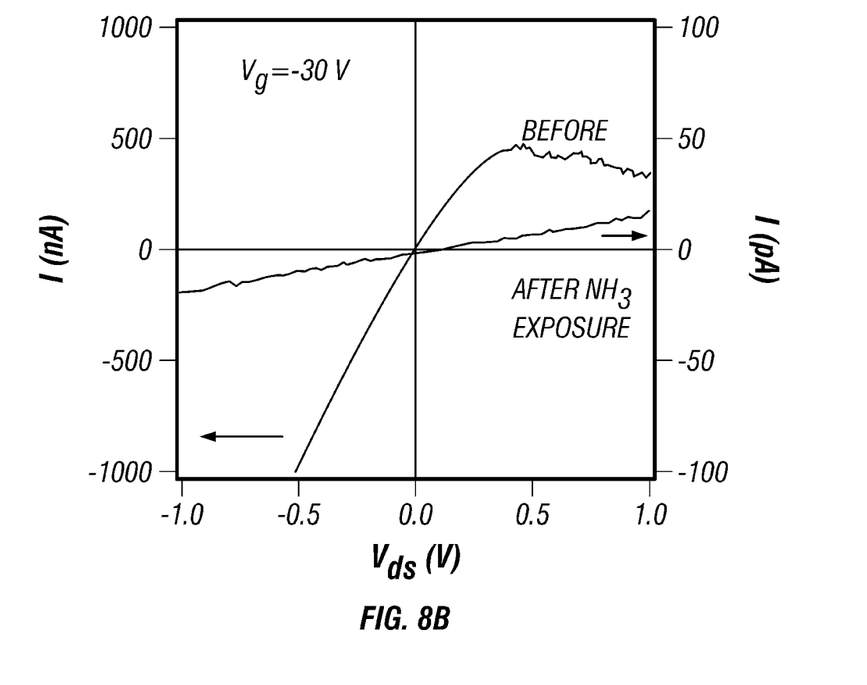

FIGS. 8A and 8B respectively show the I-V curves recorded before and after exposure to this sensed material. The "curves," showing how the I-V characteristics look before and after exposure, can be used to evaluate the presence of the species.

The zero bias resistance for this device may be 580 k ohms. After exposure, the device may show a reduction in conductance of about six orders of magnitude for a voltage of 0.3 V.

Figure 9A:
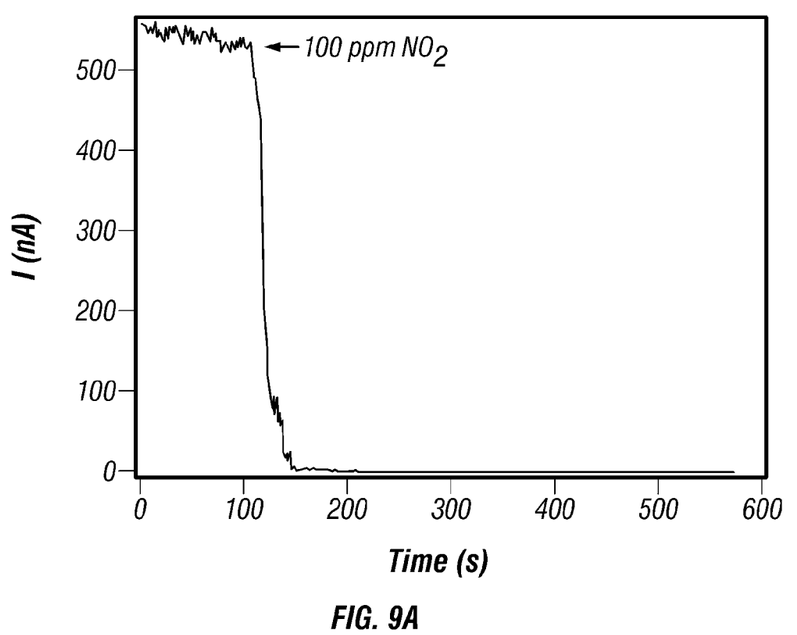
FIG. 9A and 9B show the difference between shape of response curves depending on whether a Nitro group or an amine group is present.
Figure 9B:
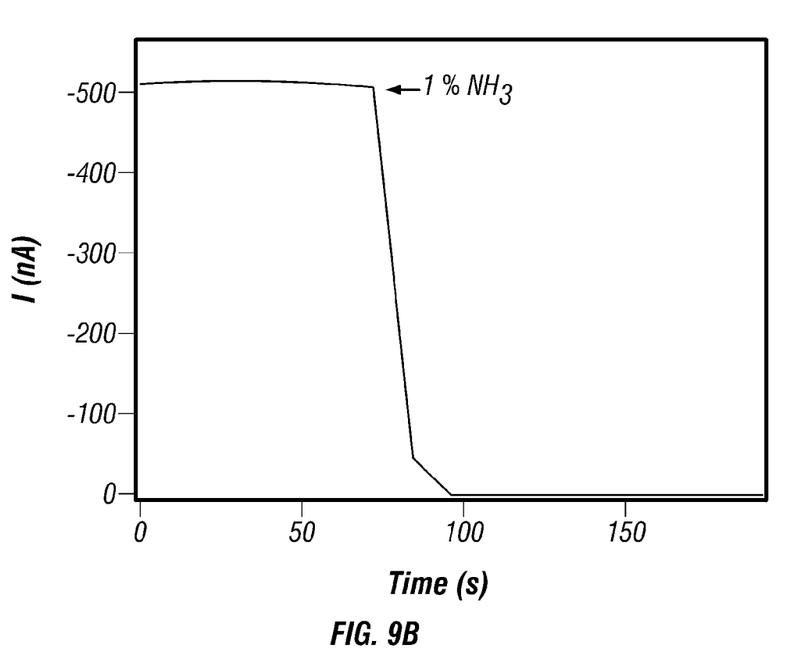

One application of this sensor is for example selectivity between different materials. FIG. 9A and 9B show how the sensor has a different electrical response to $NO_2$ as compared with $NH_3$. This response can be used to sense which material is in contact with the sensor.

Indium oxide nanowires exposed to high concentration $NH_3$ have a weakened gate effect. More specifically, the efficiency of gate bias to modify the channel conductance is weakened by the adsorbed $NH_3$ species. It is believed that this is caused by the absorbed $NH_3$ species working as charge traps. The density of oxygen vacancies along the nanowire sensors can determine the sign, amplitude, and other characteristics of the response. Chemically adsorbed $NH_3$ molecules can screen the gate electric field by operating as charge traps.

In this way, the nanowires can be used to investigate the chemical gating effect of small organic molecules with amine or nitro groups. The electron donating capability of the amine groups, and the electron withdrawing capability of the nitro groups induce changes in the nanowire conductance. This conductance can be sensed. This leads to gate threshold voltage as a result of carrier concentration variation. In addition, the absorption of the Nitro compound on partial lengths of the nanowire lead to modulated chemical gating and intra nanowire junctions exhibiting prominent rectifying behavior.

Electron donating effect of amino groups causes shift in the gate threshold voltage and an increase in conductance. Nitro groups on the other hand are highly oxidative, and withdraw electrons from the nanowires, leading to reduced carrier concentration and conduction. This can be used to distinguish between butylamine and butyl nitrate, for example, as well as detecting concentration. Based on this, nanowires may operate as biosensors for biological species containing amino or Nitro groups. One detection is for LDL cholesterol which is the major carrier of cholesterol and blood and the offending agent in coronary heart disease. For example, an average LDL particle has a hydrophobic core and a protein called apolipoprotein B-100 (apoB-100) which has a positively charge amino group (NH3+) at its outer surface.

Another aspect may form intra nanowire junctions by exposing part of the nanowire to butyl nitrite of leading to n–/n junctions and rectifying behavior with rectification ratios of approximately 400.

III. Cleansing

After exposure to the element, the device is cleansed. In an embodiment, the device is cleansed by pumping the system to vacuum, followed by ultraviolet illumination to desorb the molecules from the nanowire. Recovery under UV illumination occurs in less than 30 seconds. It is believed that the UV exposure creates electron/hole pairs in the nanowire, and that the adsorbed species are desorbed by taking one whole and then leaving the nanowire surface. This recovery mechanism works for many different adsorbed species. The Ultraviolet sterilization may be used as initialization or pretreatment. If the nanowire has been cleaned by ultraviolet illumination in a vacuum, then the conductance increases for lightly doped nanowires and decreases for heavily doped nanowires. The conductance consistently increases upon $NH_3$ exposure. In summary, the performance of the Indium oxide nanowire as ammonia sensors is affected by both the doping concentration and surface preparation. For example, the surfaces may be cleaned by ultraviolet illumination.

Although only a few embodiments have been disclosed in detail above, other modifications are possible, and this disclosure is intended to cover all such modifications, and most particularly, any modification which might be predictable to a person having ordinary skill in the art. For example, although the above describes the characterization in a field effect transistor, the properties of the nanowire can be characterized in any electrical device, including any transistor or any other device which is capable of characterizing depletion or enrichment of charge carriers on the surface of the nanowire. In addition, while the above has described the material being used as being indium oxide, it is contemplated that other metal oxide semiconductors could alternatively be used.

Also, only those claims which use the words "means for" are intended to be interpreted under 35 USC 112, sixth paragraph. Moreover, no limitations from the specification are intended to be read into any claims, unless those limitations are expressly included in the claims.

What is claimed is:

1. A method, comprising:

forming a vapor of an indium material;

using a carrying gas including oxygen to carry said vapor of the indium material in a furnace;

contacting the vapor of the indium material with a catalyst having a size of 30 nm or less;

using the catalyst to form an $In_2O_3$ nanowire of a thickness which is within 20% of the size of the catalyst;

using said nanowire to form a transistor by forming a substrate of silicon with an insulating covering, locating said nanowire on said insulating covering, forming connections to first and second ends of said nanowire as drain and source connections, and using the silicon substrate as a back gate;

characterizing conduction patterns of said transistor; and using said characterizing to determine whether a material in contact with said nanowire is electron donating or electron removing.

2. A method as in claim 1, wherein said using the catalyst comprises forming the $In_2O_3$ nanowire using a vapor-liquidsolid mechanism in which the catalyst mixed with the indium material is caused to supersaturate and nucleate.

3. A method as in claim 1, wherein said forming the vapor of the indium material comprises using a laser to evaporate indium from a solid target.

4. A method as in claim 1, further comprising using said characterizing to determine whether the material is one of an amine group or a Nitro group.

5. A method as in claim 1, further comprising using said transistor to detect the presence of a species and a concentration of the species.

6. A method as in claim 1, further comprising characterizing depletion or enrichment of charge carriers on a surface of the $In_2O_3$ nanowire to detect specified materials.

7. A method as in claim 1, further comprising sterilizing the $In_2O_3$ nanowire using ultraviolet light.

8. A method as in claim 1, wherein the $In_2O_3$ nanowire has an aspect ratio of at least 100:1 to enhance gate dependence and reduce transconductance of the transistor.

9. A method as in claim 1, wherein the transistor has a reduction in conductance of at least about five orders of magnitude after the $In_2O_3$ nanowire is in contact with the material.

10. A method as in claim 1, wherein the transistor is capable of detecting 0.5 ppm for $NO_2$ and 0.02% for $NH_3$.

* * * * *